US012400788B2

United States Patent
Diekhans et al.

(10) Patent No.: US 12,400,788 B2
(45) Date of Patent: Aug. 26, 2025

(54) DEVICE FOR INDUCTIVE ENERGY TRANSMISSION IN A HUMAN BODY AND USE OF THE DEVICE

(71) Applicant: KARDION GMBH, Stuttgart (DE)

(72) Inventors: Tobias Diekhans, Stuttgart (DE); Samuel Vasconcelos Araujo, Esslingen (DE); Michael Jiptner, Besigheim (DE)

(73) Assignee: Kardion GmbH, Stuttgart (DE)

( * ) Notice: Subject to any disclaimer, the term of this patent is extended or adjusted under 35 U.S.C. 154(b) by 53 days.

(21) Appl. No.: 18/349,710

(22) Filed: Jul. 10, 2023

(65) Prior Publication Data

US 2023/0352236 A1 Nov. 2, 2023

Related U.S. Application Data

(63) Continuation of application No. 17/090,355, filed on Nov. 5, 2020, now Pat. No. 11,699,551.

(51) Int. Cl.
| | |
|---|---|
| *H01F 38/14* | (2006.01) |
| *A61M 60/873* | (2021.01) |
| *A61M 60/876* | (2021.01) |
| *H01F 27/24* | (2006.01) |
| *H02J 50/12* | (2016.01) |

(52) U.S. Cl.
CPC ............ *H01F 38/14* (2013.01); *A61M 60/873* (2021.01); *A61M 60/876* (2021.01); *H01F 27/24* (2013.01); *H02J 50/12* (2016.02)

(58) Field of Classification Search
CPC ...................................................... H01F 38/14
See application file for complete search history.

(56) References Cited

U.S. PATENT DOCUMENTS

| | | | |
|---|---|---|---|
| 2,254,698 | A | 9/1941 | Hansen, Jr. |
| 3,085,407 | A | 4/1963 | Tomlinson |
| 3,614,181 | A | 10/1971 | Meeks |
| 3,645,268 | A | 2/1972 | Capote |
| 3,747,998 | A | 7/1973 | Klein et al. |
| 3,790,878 | A | 2/1974 | Brokaw |
| 3,807,813 | A | 4/1974 | Milligan |
| 4,441,210 | A | 4/1984 | Hochmair et al. |

(Continued)

FOREIGN PATENT DOCUMENTS

| | | |
|---|---|---|
| CA | 3 000 581 | 4/2017 |
| CN | 103143072 | 6/2013 |

(Continued)

OTHER PUBLICATIONS

Atkinson et al., "Pulse-Doppler Ultrasound and Its Clinical Application", The Yale Journal of Biology and Medicine, 1977, vol. 50, pp. 367-373.

(Continued)

*Primary Examiner* — Daniel Kessie
(74) *Attorney, Agent, or Firm* — Knobbe, Martens Olson & Bear, LLP

(57) ABSTRACT

The invention relates to a device (10) for inductive energy transmission into a human body (1), having a transmitter coil (24) and/or a receiver coil (14) having a first magnetic core (26) and a resonance or choke coil (16, 34) having a second magnetic core (32), wherein the first magnetic core (26) forms a part of the second magnetic core (32).

18 Claims, 1 Drawing Sheet

(56) References Cited

U.S. PATENT DOCUMENTS

| | | |
|---|---|---|
| 4,888,009 A | 12/1989 | Lederman et al. |
| 4,888,011 A | 12/1989 | Kung et al. |
| 4,896,754 A | 1/1990 | Carlson et al. |
| 5,000,177 A | 3/1991 | Hoffmann et al. |
| 5,195,877 A | 3/1993 | Kletschka |
| 5,289,821 A | 3/1994 | Swartz |
| 5,443,503 A | 8/1995 | Yamane |
| 5,599,173 A | 2/1997 | Chen et al. |
| 5,613,935 A | 3/1997 | Jarvik |
| 5,629,661 A | 5/1997 | Ooi et al. |
| 5,690,674 A | 11/1997 | Diaz |
| 5,702,430 A | 12/1997 | Larson, Jr. et al. |
| 5,713,954 A | 2/1998 | Rosenberg et al. |
| 5,766,207 A | 6/1998 | Potter et al. |
| 5,814,900 A * | 9/1998 | Esser ............ H04B 5/00 307/104 |
| 5,843,141 A | 12/1998 | Bischoff et al. |
| 5,888,242 A | 3/1999 | Antaki et al. |
| 6,053,873 A | 4/2000 | Govari et al. |
| 6,058,958 A | 5/2000 | Benkowski et al. |
| 6,149,405 A | 11/2000 | Abe et al. |
| 6,212,430 B1 | 4/2001 | Kung et al. |
| 6,224,540 B1 | 5/2001 | Lederman et al. |
| 6,254,359 B1 | 7/2001 | Aber |
| 6,264,601 B1 | 7/2001 | Jassawalla et al. |
| 6,324,430 B1 | 11/2001 | Zarinetchi et al. |
| 6,324,431 B1 | 11/2001 | Zarinetchi et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,442,434 B1 | 8/2002 | Zarinetchi et al. |
| 6,445,956 B1 | 9/2002 | Laird et al. |
| 6,471,713 B1 | 10/2002 | Vargas et al. |
| 6,496,733 B2 | 12/2002 | Zarinetchi et al. |
| 6,508,756 B1 | 1/2003 | Kung et al. |
| 6,516,227 B1 | 2/2003 | Meadows et al. |
| 6,527,698 B1 | 3/2003 | Kung et al. |
| 6,530,876 B1 | 3/2003 | Spence |
| 6,540,658 B1 | 4/2003 | Fasciano et al. |
| 6,553,263 B1 | 4/2003 | Meadows et al. |
| 6,561,975 B1 | 5/2003 | Pool et al. |
| 6,592,620 B1 | 7/2003 | Lancisi et al. |
| 6,979,338 B1 | 12/2005 | Loshakove et al. |
| 7,062,331 B2 | 6/2006 | Zarinetchi et al. |
| 7,070,398 B2 | 7/2006 | Olsen et al. |
| 7,155,291 B2 | 12/2006 | Zarinetchi et al. |
| 7,160,243 B2 | 1/2007 | Medvedev |
| 7,338,521 B2 | 3/2008 | Antaki et al. |
| 7,513,864 B2 | 4/2009 | Kantrowitz et al. |
| 7,520,850 B2 | 4/2009 | Brockway |
| 7,762,941 B2 | 7/2010 | Jarvik |
| 7,794,384 B2 | 9/2010 | Sugiura et al. |
| 7,819,916 B2 | 10/2010 | Yaegashi |
| 7,942,805 B2 | 5/2011 | Shambaugh, Jr. |
| 7,959,551 B2 | 6/2011 | Jarvik |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,231,519 B2 | 7/2012 | Reichenbach et al. |
| 8,461,817 B2 | 6/2013 | Martin et al. |
| 8,489,200 B2 | 7/2013 | Zarinetchi et al. |
| 8,608,635 B2 | 12/2013 | Yomtov et al. |
| 8,612,002 B2 | 12/2013 | Faltys et al. |
| 8,620,447 B2 | 12/2013 | D'Ambrosio et al. |
| 8,766,788 B2 | 7/2014 | D'Ambrosio |
| 8,827,890 B2 | 9/2014 | Lee et al. |
| 8,862,232 B2 | 10/2014 | Zarinetchi et al. |
| 8,870,739 B2 | 10/2014 | LaRose et al. |
| 8,900,114 B2 | 12/2014 | Tansley et al. |
| 8,961,389 B2 | 2/2015 | Zilbershlag |
| 9,002,468 B2 | 4/2015 | Shea et al. |
| 9,002,469 B2 | 4/2015 | D'Ambrosio |
| 9,071,182 B2 | 6/2015 | Yoshida et al. |
| 9,220,826 B2 | 12/2015 | D'Ambrosio |
| 9,283,314 B2 | 3/2016 | Prasad et al. |
| 9,381,286 B2 | 7/2016 | Spence et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,539,094 B2 | 1/2017 | Dale et al. |
| 9,561,362 B2 | 2/2017 | Malinowski |
| 9,569,985 B2 | 2/2017 | Alkhatib et al. |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,800,172 B1 | 10/2017 | Leabman |
| 9,833,314 B2 | 12/2017 | Corbett |
| 9,833,611 B2 | 12/2017 | Govea et al. |
| 9,848,899 B2 | 12/2017 | Sliwa et al. |
| 9,974,894 B2 | 5/2018 | Morello |
| 10,143,571 B2 | 12/2018 | Spence et al. |
| 10,463,508 B2 | 11/2019 | Spence et al. |
| 10,732,583 B2 | 8/2020 | Rudser |
| 10,944,293 B2 | 3/2021 | Nakao |
| 11,000,282 B2 | 5/2021 | Schuelke et al. |
| 11,056,878 B2 | 7/2021 | Gao et al. |
| 11,065,437 B2 | 7/2021 | Aber et al. |
| 11,103,715 B2 | 8/2021 | Fort |
| 11,110,265 B2 | 9/2021 | Johnson |
| 11,179,559 B2 | 11/2021 | Hansen |
| 11,224,737 B2 | 1/2022 | Petersen et al. |
| 11,291,826 B2 | 4/2022 | Tuval et al. |
| 11,316,371 B1 | 4/2022 | Partovi et al. |
| 11,317,988 B2 | 5/2022 | Hansen et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,641 B2 | 7/2022 | Nguyen et al. |
| 11,406,483 B2 | 8/2022 | Wirbisky et al. |
| 11,406,520 B2 | 8/2022 | Lam |
| 11,406,802 B2 | 8/2022 | DeGraaf et al. |
| 11,413,443 B2 | 8/2022 | Hodges et al. |
| 11,413,444 B2 | 8/2022 | Nix et al. |
| 11,439,806 B2 | 9/2022 | Kimball et al. |
| 11,471,692 B2 | 10/2022 | Aghassian et al. |
| 11,497,906 B2 | 11/2022 | Grace et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,529,508 B2 | 12/2022 | Jablonsk et al. |
| 11,583,671 B2 | 2/2023 | Nguyen et al. |
| 11,596,727 B2 | 3/2023 | Siess et al. |
| 11,602,624 B2 | 3/2023 | Siess et al. |
| 11,682,924 B2 | 6/2023 | Hansen et al. |
| 11,689,057 B2 | 6/2023 | Hansen |
| 11,699,551 B2 | 7/2023 | Diekhans et al. |
| 11,745,005 B2 | 9/2023 | Delgado, III |
| 11,752,354 B2 | 9/2023 | Stotz et al. |
| 11,804,767 B2 | 10/2023 | Vogt et al. |
| 11,881,721 B2 | 1/2024 | Araujo et al. |
| 11,996,699 B2 | 5/2024 | Vasconcelos Araujo et al. |
| 12,102,835 B2 | 10/2024 | Stotz et al. |
| 2001/0016686 A1 | 8/2001 | Okada et al. |
| 2002/0177324 A1 | 11/2002 | Metzler |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1 | 1/2005 | Chen et al. |
| 2005/0107658 A1 | 5/2005 | Brockway |
| 2005/0107847 A1 | 5/2005 | Gruber et al. |
| 2006/0004423 A1 | 1/2006 | Boveja et al. |
| 2006/0190036 A1 | 8/2006 | Wendel et al. |
| 2006/0196277 A1 | 9/2006 | Allen et al. |
| 2007/0129767 A1 | 6/2007 | Wahlstrand |

(56) References Cited

U.S. PATENT DOCUMENTS

| | | |
|---|---|---|
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0211455 A1 | 9/2008 | Park et al. |
| 2008/0266922 A1 | 10/2008 | Mumtaz et al. |
| 2009/0010462 A1 | 1/2009 | Ekchian et al. |
| 2009/0024042 A1 | 1/2009 | Nunez et al. |
| 2009/0134711 A1 | 5/2009 | Issa et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0010582 A1 | 1/2010 | Carbunaru |
| 2010/0191035 A1 | 7/2010 | Kang et al. |
| 2010/0219967 A1 | 9/2010 | Kaufmann |
| 2010/0280568 A1 | 11/2010 | Bulkes et al. |
| 2010/0312310 A1* | 12/2010 | Meskens ............ H02J 50/005 607/61 |
| 2010/0331918 A1 | 12/2010 | Digiore et al. |
| 2010/0331920 A1 | 12/2010 | Digiore et al. |
| 2011/0071336 A1 | 3/2011 | Yomtov |
| 2011/0137394 A1 | 6/2011 | Lunsford et al. |
| 2011/0224720 A1 | 9/2011 | Kassab et al. |
| 2012/0019201 A1 | 1/2012 | Peterson |
| 2012/0022645 A1 | 1/2012 | Burke |
| 2012/0050931 A1 | 3/2012 | Terry et al. |
| 2012/0112543 A1 | 5/2012 | van Wageningen et al. |
| 2012/0158074 A1 | 6/2012 | Hall |
| 2012/0212178 A1 | 8/2012 | Kim |
| 2012/0235633 A1 | 9/2012 | Kesler et al. |
| 2013/0069651 A1 | 3/2013 | Lumiani |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0194058 A1 | 7/2014 | Lee et al. |
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2015/0008755 A1 | 1/2015 | Sone |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1 | 10/2015 | Rudser et al. |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095968 A1 | 4/2016 | Rudser |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0231717 A1 | 8/2017 | Forsell |
| 2017/0271919 A1 | 9/2017 | Von Novak, III et al. |
| 2017/0275799 A1 | 9/2017 | Chen |
| 2017/0288448 A1 | 10/2017 | Kranz et al. |
| 2017/0303375 A1 | 10/2017 | Woodhead |
| 2017/0353053 A1 | 12/2017 | Muratov |
| 2017/0354812 A1 | 12/2017 | Callaghan et al. |
| 2018/0078329 A1 | 3/2018 | Hansen et al. |
| 2018/0194236 A1 | 7/2018 | Elshaer et al. |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2018/0287405 A1 | 10/2018 | Govindaraj |
| 2018/0316209 A1 | 11/2018 | Gliner |
| 2019/0004037 A1 | 1/2019 | Zhang et al. |
| 2019/0060543 A1 | 2/2019 | Khanal et al. |
| 2019/0068004 A1 | 2/2019 | Louis |
| 2019/0097447 A1 | 3/2019 | Partovi |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0057804 A1 | 2/2021 | Wenning |
| 2021/0143688 A1 | 5/2021 | Agrawal et al. |
| 2021/0290931 A1 | 9/2021 | Baumbach |
| 2021/0322011 A1 | 10/2021 | Schuelke et al. |
| 2021/0336484 A1 | 10/2021 | Araujo et al. |
| 2021/0339009 A1 | 11/2021 | Stotz et al. |
| 2021/0351628 A1 | 11/2021 | Araujo et al. |
| 2021/0379360 A1 | 12/2021 | Schellenberg |
| 2021/0386990 A1 | 12/2021 | Stotz et al. |
| 2021/0393944 A1 | 12/2021 | Wenning |
| 2021/0399582 A1 | 12/2021 | Araujo et al. |
| 2022/0080184 A1 | 3/2022 | Clifton et al. |
| 2022/0080185 A1 | 3/2022 | Clifton et al. |
| 2022/0320901 A1 | 10/2022 | Araujo et al. |
| 2022/0407403 A1 | 12/2022 | Vogt et al. |
| 2023/0191141 A1 | 6/2023 | Wenning et al. |
| 2023/0381526 A1 | 11/2023 | Stotz et al. |
| 2024/0269459 A1 | 8/2024 | Schellenberg et al. |

FOREIGN PATENT DOCUMENTS

| | | |
|---|---|---|
| CN | 103942511 | 7/2014 |
| CN | 104274873 | 1/2015 |
| CN | 104888293 | 3/2017 |
| CN | 106776441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2016 225 862 | 6/2017 |
| DE | 10 2016 203 172 | 8/2017 |
| DE | 10 2017 213 475 | 2/2019 |
| DE | 10 2018 204 604 | 10/2019 |
| DE | 10 2018 204 610 | 10/2019 |
| DE | 10 2018 206 714 | 11/2019 |
| DE | 10 2018 206 724 | 11/2019 |
| DE | 10 2018 206 725 | 11/2019 |
| DE | 10 2018 206 727 | 11/2019 |
| DE | 10 2018 206 731 | 11/2019 |
| DE | 10 2018 206 750 | 11/2019 |
| DE | 10 2018 206 754 | 11/2019 |
| DE | 10 2018 206 758 | 11/2019 |
| DE | 10 2018 222 505 | 6/2020 |
| EP | 0 930 086 | 7/1999 |
| EP | 2 752 209 | 7/2014 |
| EP | 2 782 210 | 9/2014 |
| EP | 2 859 911 | 4/2015 |
| EP | 2 966 753 | 1/2016 |
| EP | 2 454 799 | 9/2016 |
| EP | 2 709 689 | 4/2017 |
| EP | 3 220 505 | 9/2017 |
| EP | 3 536 360 | 9/2019 |
| EP | 3 357 523 | 1/2021 |
| EP | 3 423 126 | 2/2021 |
| EP | 3 490 628 | 2/2021 |

(56) References Cited

FOREIGN PATENT DOCUMENTS

| | | |
|---|---|---|
| EP | 3 198 677 | 3/2021 |
| EP | 3 248 647 | 3/2021 |
| EP | 3 436 106 | 3/2021 |
| EP | 3 509 661 | 3/2021 |
| EP | 3 528 863 | 3/2021 |
| EP | 3 436 105 | 4/2021 |
| EP | 3 116 407 | 5/2021 |
| EP | 3 131 600 | 6/2021 |
| EP | 3 827 876 | 6/2021 |
| EP | 2 608 731 | 7/2021 |
| EP | 2 599 510 | 10/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| EP | 3 497 775 | 7/2022 |
| EP | 3 711 788 | 8/2022 |
| EP | 2 654 883 | 9/2022 |
| EP | 3 485 819 | 9/2022 |
| EP | 3 600 477 | 10/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 946 511 | 4/2023 |
| EP | 3 826 104 | 5/2023 |
| JP | H11-178249 | 7/1999 |
| JP | 4706886 | 6/2011 |
| JP | 2013-013216 | 1/2013 |
| JP | 2018-046708 | 3/2018 |
| KR | 10-1185112 | 9/2012 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2011/007300 | 1/2011 |
| WO | WO 2012/147061 | 11/2012 |
| WO | WO 2013/164831 | 11/2013 |
| WO | WO 2015/152732 | 10/2015 |
| WO | WO 2017/021846 | 2/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |
| WO | WO 2023/076869 | 5/2023 |

OTHER PUBLICATIONS

Leguy et al., "Assessment of Blood Volume Flow in Slightly Curved Arteries from a Single Velocity Profile", Journal of Biomechanics, 2009, pp. 1664-1672.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

Vieli, A., "Doppler Flow Determination", BJA: British Journal of Anaesthesia, 1988, vol. 60, pp. 107S-112S.

* cited by examiner

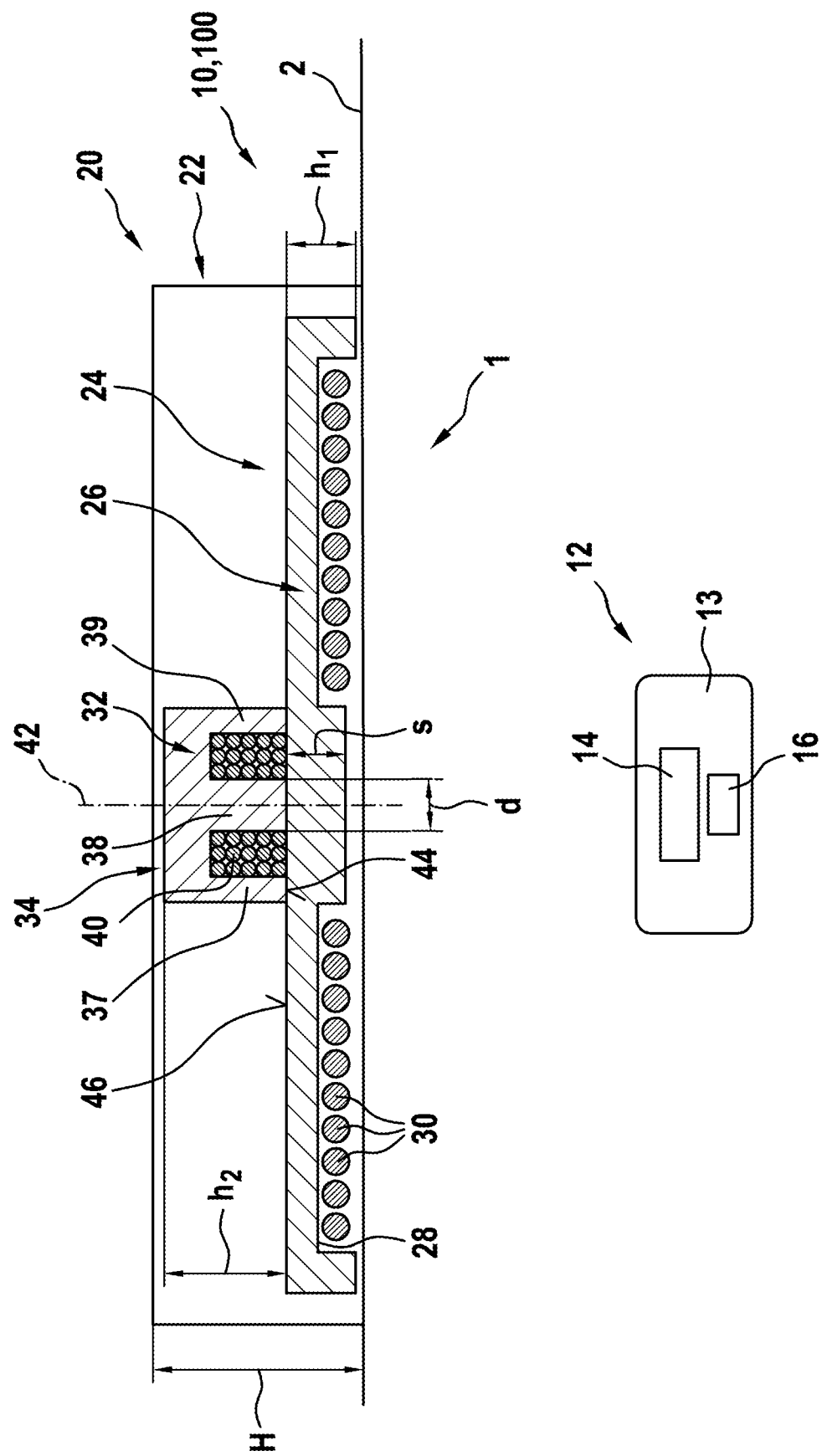

DEVICE FOR INDUCTIVE ENERGY TRANSMISSION IN A HUMAN BODY AND USE OF THE DEVICE

BACKGROUND

Field

The invention relates to a device for inductive energy transmission into a human body. The invention further relates to the use of a device according to the invention.

Medical technology uses devices for inductive energy transmission, in which a transmitter unit disposed outside a human body comprises a transmitter coil, the magnetic field of which induces energy in the receiver coil of a receiver unit disposed [in] the human body, which at least indirectly serves to charge a battery disposed in the human body. Such a system is known as a so-called VAD (ventricular assist device) system used to operate a pump that supports the heart of a patient (DE 10 2016 106 683 A1).

For such a device, and this applies to both the receiver unit and the transmitter unit, it is essential that it is configured in as compact a manner as possible. On the one hand, in terms of the receiver unit, this minimizes the space required in the body for the receiver unit, while on the other hand, in terms of the transmitter unit, it increases the wearing comfort of such a transmitter unit under the patient's clothing. The transmitter unit or the receiver unit furthermore typically comprise a housing, in which the components of the respective unit are disposed. It is also known that, in addition to the transmitter coil or the receiver coil, an electronic circuit is required for the operation of said coils, which typically also comprises a so-called resonance or choke coil. Like the transmitter coil or the receiver coil, such a resonance or choke coil comprises a magnetic core and a wire winding that interacts with the magnetic core. In the case of the resonance or choke coil, this is typically a component of a resonance circuit and, in the state of the art, is always disposed discretely, i.e. separately from the transmitter coil or receiver coil, on a circuit carrier (circuit board) together with other electronic components. The separate arrangement and configuration of the magnetic cores for the transmitter coil or receiver coil and for the resonance or choke coil results in an increase of the overall height of the transmitter unit or receiver unit, in particular with regard to the respective magnetic cores, because the resonance or choke coil is disposed above or below the level of the transmitter coil or receiver coil and thus also affects the overall height of the housing of the transmitter unit or receiver unit.

DISCLOSURE OF THE INVENTION

Summary

The device according to the invention for inductive energy transmission having the features of Claim 1 has the advantage that it enables a particularly compact arrangement of the transmitter coil or receiver coil and the resonance or choke coil in the transmitter unit or the receiver unit.

The invention is based on the idea of using or configuring a part of the magnetic core of the transmitter coil or the receiver coil simultaneously as a part of the magnetic core of the resonance or choke coil or vice versa. This not only saves material for the magnetic cores, but also enables a particularly compact arrangement of the two magnetic cores relative to one another.

Advantageous further developments of the device for inductive energy transmission into a human body according to the invention are presented in the subclaims.

In a first structural configuration of the device, it is provided that the first magnetic core (of the transmitter or receiver coil) is disposed in direct contact with an end face of the second magnetic core (of the resonance or choke coil).

In order to fulfill the intended functionality, it is furthermore provided in a preferred structural configuration that the transmitter coil or the receiver coil comprises wire windings which are disposed concentrically to one another and the resonance or choke coil comprises second wire windings which are disposed concentrically to one another, and that the first wire windings are disposed radially outside the second wire windings.

The last-mentioned configuration in particular leads to a geometric arrangement, in which the resonance or choke coil is disposed concentrically to a longitudinal axis of the first magnetic core.

A structural arrangement or configuration of the two coils (transmitter coil and receiver coil or resonance or choke coil) as described thus far in particular enables a desired decoupling of the transmitter and the receiver coil with the resonance or choke coil due to both the selected topology and the design of the transmitter or receiver coil itself. The transmitter coil and the receiver coil in particular have a very low coupling factor to the resonance or choke coil, because the (magnetic) fields of the transmitter coil or receiver coil are enclosed on one side by the ferrite core. The return of the magnetic fields on the other side then takes place via the air over a longer distance and thus leads to the aforementioned low coupling. The structural arrangement of the coils as described thus far typically has a very low coupling factor of typically up to about 0.05.

Another preferred structural configuration provides that the first magnetic core is disc-shaped and has at least one groove-like recess which extends radially around the longitudinal axis for receiving first wire windings of the transmitter or receiver coil.

In particular in the last-mentioned design, it is further provided that the resonance or choke coil is disposed on the side of the at least one recess which faces away from the first wire windings.

To positively affect the saturation of the core material of the magnetic core of the resonance or choke coil and for the purpose of optimal guidance of the magnetic field lines, it is also advantageous if, in the region of contact with the second magnetic core, the first magnetic core has a wall thickness which corresponds to the wall thickness of a middle leg of the E-core of the second magnetic core.

The invention further also includes the use of a device for energy transmission into a human body according to the invention as described thus far, in particular as a component of a VAD system.

Further advantages, features and details of the invention emerge from the following description of preferred design examples and with reference to the drawing.

BRIEF DESCRIPTION OF THE DRAWING

The only FIGURE shows a schematic illustration of a device for inductive energy transmission into a human body.

DETAILED DESCRIPTION

The device 10 shown in the only FIGURE is in particular configured as a component of a so-called VAD system 100, wherein the VAD system 100 comprises a pump for supporting the heart function of a patient that is operated or supplied with energy via a not-depicted battery. This battery is charged by means of the device 10.

The device 10 comprises a receiver unit 12 that is disposed in a human body 1 and comprises a housing 13, in which a receiver coil 14, which is shown in the illustration of the FIGURE in a highly simplified manner, is disposed. The receiver coil 14 is used for at least indirect charging of said battery, for example via not-depicted wire connections to the battery and a not-depicted electronic circuit. In addition to the receiver coil 14, the receiver unit 12 further comprises a choke coil 16, which is likewise shown purely schematically and is not a component of a receiving oscillator circuit.

The receiver unit 12 interacts with a transmitter unit 20 disposed outside the body 1. As an example, the transmitter unit 20 comprises a housing 22 which, on the one hand, can be positioned in at least indirect contact with the skin 2 of the body 1 and in alignment with the receiver unit 12 and, on the other hand, comprises a transmitter coil 24 in its interior. The transmitter coil 24 consists of a disc-shaped first magnetic core 26, which comprises a radially circumferential, groove-like recess 28 on the side facing the receiver unit 12. First wire windings 30, which are disposed concentrically to one another around a longitudinal axis 42 of the first magnetic core 26, are disposed in the region of the recess 28 and serve to produce a not-depicted magnetic field in order to induce electrical energy in the receiver coil 12 which is used to charge said battery.

As an example, the transmitter coil 24 has a height $h_1$. On the side of the first magnetic core 26 facing away from the receiver unit 12, a second magnetic core 32 is disposed as part of a resonance or choke coil 34. The second magnetic core 32 is configured in the form of an E-magnetic core 32. Second wire windings 40 of the resonance or choke coil 34 are concentrically wound around a (central) middle leg 38 of the second magnetic core 36.

As can be seen from the illustration of the FIGURE, the middle leg 38 is also disposed concentrically to the longitudinal axis 42 of the first magnetic core 26. The second wire windings 40 furthermore extend radially inside the first wire windings 30 of the transmitter coil 24.

With its three legs 37 to 39, the end face 44 of the second magnetic core 36 facing the first magnetic core 26 directly abuts the end face 46 of the first magnetic core 26. The illustration of the FIGURE also shows that, in the region in which the second magnetic core 32 and the first magnetic core 26 overlap, the thickness d of the middle leg 38 of the second magnetic core 32 corresponds to the wall thickness s of the first magnetic core 26. The second magnetic core 32 has a height $h_2$. The illustration of the FIGURE further shows that the total height H of the housing 22 of the transmitter unit 20 substantially depends on or is determined by the sum of the two heights $h_1$ and $h_2$ of the two magnetic cores 26 and 32.

The device 10 as described thus far can be changed or modified in many ways without departing from the idea of the invention. It is in particular noted that the specific configuration of the transmitter coil 24 and the resonance or choke coil 34, or the magnetic cores 26, 32 thereof, has been described on the basis of the transmitter unit 20. It is just as possible for the described structure to be provided in the same way in the region of the receiver unit 12. This likewise results in a minimization of the overall height of the housing 13 of the receiver unit 12.

What is claimed is:

1. A device for inductively transmitting energy into or receiving energy within a human body, the device comprising:
   a first coil including a first magnetic core, wherein the first magnetic core has an end face and at least one leg extending away from a side opposite the end face and is configured to receive a plurality of wire windings opposite the end face and around the at least one leg, and
   a second coil including a second magnetic core, the second magnetic core comprising three legs abutting the end face of the first magnetic core, wherein the second coil includes at least one recess extending radially around a middle leg of the three legs, the at least one recess configured to receive a plurality of wire windings,
   wherein the first magnetic core and the second magnetic core have E-shaped cross-sections facing in a same direction, and wherein a width of the first magnetic core disposed in direct contact with the second magnetic core corresponds to a width of the middle leg of the second magnetic core.

2. The device according to claim 1, wherein the plurality of wire windings of the second coil wind concentrically around the middle leg of the second magnetic core.

3. The device according to claim 1, wherein the first coil comprises a plurality of first wire windings disposed concentrically relative to one another, wherein the second coil comprises a plurality of second wire windings disposed concentrically relative to one another, and wherein the plurality of first wire windings are disposed radially outside the plurality of second wire windings.

4. The device according to claim 1, wherein the second coil is disposed concentrically to a longitudinal axis of the first magnetic core.

5. The device according to claim 1, wherein the first magnetic core is disc-shaped.

6. The device according to claim 5, wherein the first magnetic core comprises a radially circumferential recess.

7. The device according to claim 1, further comprising a housing surrounding the first coil and the second coil, a height of the housing being equal to a height of the first coil and a height of the second coil.

8. A method for inductively transmitting energy, the method comprising:
   inductively transmitting energy using a transmitter device and a receiver device, wherein at least one of the transmitter device and the receiver device comprises:
   a first coil including a first magnetic core, wherein the first magnetic core has an end face and at least one leg extending away from a side opposite the end face and is configured to receive a plurality of wire windings opposite the end face and around the at least one leg, and
   a second coil including a second magnetic core, the second magnetic core comprising three legs abutting the end face of the first magnetic core, wherein the second coil includes at least one recess extending radially around a middle leg of the three legs, the at least one recess configured to receive a plurality of wire windings,
   wherein the first magnetic core and the second magnetic core have E-shaped cross-sections facing in a same direction, and wherein a width of the first magnetic core disposed in direct contact with the second magnetic core corresponds to a width of the middle leg of the second magnetic core.

9. The method of claim 8, wherein at least one of the transmitter device and the receiver device further comprises a housing, wherein the housing is in at least indirect contact with skin of a human body.

10. The method of claim 8, wherein the transmitter device inductively transmits energy and the receiver device inductively receives energy.

11. The method of claim 10, wherein the energy received at the receiver device is used for charging a battery in communication with the receiver device.

12. A system for inductive energy transmission, the system comprising:
   a first device including a first coil and a second coil; and
   a second device,
   wherein the first coil includes a first magnetic core, wherein the first magnetic core has an end face and at least one leg extending away from a side opposite the end face and is configured to receive a plurality of wire windings opposite the end face and around the at least one leg and wherein the second coil includes a second magnetic core,
   wherein the second magnetic core comprises three legs abutting the end face of the first magnetic core, wherein the second coil includes at least one recess extending radially around a middle leg of the three legs, the at least one recess configured to receive a plurality of wire windings,
   wherein the first magnetic core and the second magnetic core have E-shaped cross-sections facing in a same direction and
   wherein the first and second devices are disposed in alignment on opposite sides of skin of a body to transfer energy into the body, and wherein a width of the first magnetic core disposed in direct contact with the second magnetic core corresponds to a width of the middle leg of the second magnetic core.

13. The system of claim 12, wherein the plurality of wire windings of the second coil wind concentrically around the middle leg of the second magnetic core.

14. The system of claim 12, wherein the first coil comprises a plurality of first wire windings disposed concentrically relative to one another, wherein the second coil comprises a plurality of second wire windings disposed concentrically relative to one another, and wherein the plurality of first wire windings are disposed radially outside the plurality of second wire windings.

15. The system of claim 12, wherein the second coil is disposed concentrically to a longitudinal axis of the first magnetic core.

16. The system according to claim 12, further comprising a housing surrounding the first coil and the second coil, a height of the housing equal to a height of the first coil and a height of the second coil.

17. The system according to claim 12, wherein the first magnetic core is disc shaped.

18. The system according to claim 17, wherein the first magnetic core comprises a radially circumferential recess.

* * * * *